(12) United States Patent
Giles

(10) Patent No.: US 9,981,933 B2
(45) Date of Patent: May 29, 2018

(54) DETERGENT COMPOSITIONS

(71) Applicant: INNOSPEC LIMITED, Ellesmere Port, Cheshire (GB)

(72) Inventor: Matthew Robert Giles, Chester (GB)

(73) Assignee: INNOSPEC LIMITED, Cheshire (GB)

(*) Notice: Subject to any disclaimer, the term of this patent is extended or adjusted under 35 U.S.C. 154(b) by 61 days.

(21) Appl. No.: 15/032,199

(22) PCT Filed: Nov. 3, 2014

(86) PCT No.: PCT/GB2014/053263
§ 371 (c)(1),
(2) Date: Apr. 26, 2016

(87) PCT Pub. No.: WO2015/063515
PCT Pub. Date: May 7, 2015

(65) Prior Publication Data
US 2016/0264542 A1  Sep. 15, 2016

(30) Foreign Application Priority Data
Nov. 1, 2013 (GB) .................................. 1319379.2

(51) Int. Cl.
| | | |
|---|---|---|
| *C11D 1/14* | (2006.01) | |
| *C11D 1/26* | (2006.01) | |
| *C07D 307/62* | (2006.01) | |
| *A61K 8/46* | (2006.01) | |
| *A61K 8/49* | (2006.01) | |
| *A61Q 5/02* | (2006.01) | |
| *A61Q 19/10* | (2006.01) | |
| *C11D 1/12* | (2006.01) | |
| *C11D 1/10* | (2006.01) | |
| *C11D 1/86* | (2006.01) | |
| *C11D 3/30* | (2006.01) | |
| *C11D 3/28* | (2006.01) | |
| *C11D 1/58* | (2006.01) | |
| *C07D 415/00* | (2006.01) | |

(52) U.S. Cl.
CPC .............. *C07D 307/62* (2013.01); *A61K 8/49* (2013.01); *A61K 8/4973* (2013.01); *A61Q 5/02* (2013.01); *A61Q 19/10* (2013.01); *C07D 415/00* (2013.01); *C11D 1/10* (2013.01); *C11D 1/126* (2013.01); *C11D 1/14* (2013.01); *C11D 1/146* (2013.01); *C11D 1/58* (2013.01); *C11D 1/86* (2013.01); *C11D 3/28* (2013.01); *C11D 3/30* (2013.01)

(58) Field of Classification Search
CPC .. C11D 1/14; C11D 1/146; C11D 1/26; C11D 3/2093; C11D 3/2096; C07D 307/62; A61K 8/46; A61K 8/49; A61K 8/4973; A61Q 5/02; A61Q 19/10
See application file for complete search history.

(56) References Cited

U.S. PATENT DOCUMENTS

| | | |
|---|---|---|
| 2,368,435 A | 1/1945 | Wickard |
| 2,694,066 A | 11/1954 | Reed |
| 3,436,227 A | 4/1969 | Bergeron et al. |
| 6,130,329 A | 10/2000 | Ogawa et al. |
| 2004/0023935 A1 | 2/2004 | Banerjee et al. |
| 2015/0126368 A1* | 5/2015 | Kageyama ............. A01N 43/08 504/128 |

FOREIGN PATENT DOCUMENTS

| | | | | |
|---|---|---|---|---|
| EP | 0571086 A1 | 11/1993 | | |
| EP | 0875246 A1 | 11/1998 | | |
| EP | 0875514 A1 | 11/1998 | | |
| EP | 2478768 | * | 7/2012 | ............. A01N 43/08 |
| EP | 2478768 A1 | 7/2012 | | |
| JP | 61151107 | * | 7/1986 | ............... A61L 7/00 |
| JP | S61151107 A | 7/1986 | | |

(Continued)

OTHER PUBLICATIONS

Combined Search Report and Examination Report dated Jul. 30, 2015 for GB1419586.1 (4 pgs.).
Further Search Report under Section 17 dated Jul. 24, 2014 for GB1319379.2 (claim 3 in full).
Further Search Report under Section 17 dated Jul. 24, 2014 for GB1319379.2 (claim 4 in full).
ntemational Search Report and Written Opinion dated May 3, 2016 for PCT/GB2014/053263.
Cousins et al., "Synthesis of 6-Fatty Acid Esters of L-Ascorbic Acid", Journal of the American Oil Chemists' Society, vol. 54, pp. 308-312.
Kunz, H.A. Comparative investigations on the oxidation of pyruvate in liver and brain mitochondria. Biochimica et Biophysica Acta, vol. 28 (1958), pp. 104-107.
Stern, M. et al. Evaluation of EpiOcular (TM) Tissue Model as an Alternative to the Draize Eye Irritation Test. Toxicology in Vitro (Aug. 1998) 12(4): 455-461.

(Continued)

*Primary Examiner* — Brian P Mruk
(74) *Attorney, Agent, or Firm* — Burns & Levinson LLP; Janine M. Susan

(57) ABSTRACT

A surfactant component comprising a compound of formula (I): (I) wherein $R^1$ is a $C_5$ to $C_{39}$ alkyl or alkenyl group and $R^2$ is a group of formula (a) wherein one of W, X, Y and Z is a covalent bond and the remaining groups are independently selected from H, M, $SO_3M$ and a further group of formula $R^1CO$ provided at least one of W, X, Y and Z is $SO_3M$; and each M is independently a hydrogen ion, an ammonium ion or a metal ion.

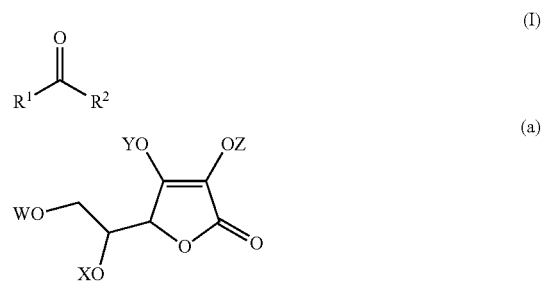

15 Claims, No Drawings

(56) References Cited

FOREIGN PATENT DOCUMENTS

| JP | H11199448 A | 7/1999 |
| JP | 32000973 B | 6/2001 |
| WO | 199409763 A1 | 5/1994 |
| WO | 9505154 A1 | 2/1995 |
| WO | 03010173 A1 | 2/2003 |
| WO | 2005075623 A1 | 8/2005 |
| WO | 2007013633 A1 | 2/2007 |
| WO | 2007066832 A1 | 6/2007 |
| WO | 2014013743 A1 | 1/2014 |
| WO | 2014013744 A1 | 1/2014 |
| WO | WO 2014/013743 * | 1/2014 ............. A01N 43/08 |

OTHER PUBLICATIONS

CFTA Cosmetic Ingredient Handbook (2nd Ed). The Cosmetic Toiletries and Fragrance Association, Inc. (Jun. 1992), p. 27.
Database WPI, Week 198634, Thomson Scientific, AN 1986-221278, XP002733038.
Cousins, R.C. et al. Synthesis of 6-fatty acid esters of L-ascorbic acid. J Am Oil Chem Soc. (Aug. 1977) 54(8):308-12.
International Search Report and Written Opinion dated May 12, 2014 for PCT/GB2014/053263.
Search Report under Section 17 dated May 8, 2014 for GB1319379.2.
Further Search Report under Section 17 dated Jul. 24, 2014 for GB1319372.2 (claim 3 in full).
Further Search Report under Section 17 dated Jul. 24, 2014 for GB1319372.2 (claim 4 in full).

* cited by examiner

DETERGENT COMPOSITIONS

CROSS-REFERENCE TO RELATED APPLICATIONS

This application is a U.S. national stage application under 35 U.S.C. 371 co-pending International Application No. PCT/GB2014/053263 filed on Nov. 3, 2014 and entitled DETERGENT COMPOSITIONS, which in turn claims priority to Great Britain Patent Application No. 1319379.2, filed on Nov. 1, 2013, the contents of which are incorporated by reference herein in their entirety for all purposes.

The present invention relates to new surfactant compounds, to compositions comprising such compounds and to methods and uses relating thereto.

In particular the present invention relates to surfactant compounds which have low irritancy to skin and eyes.

A very large number of surfactant compounds are known having a range of different properties and uses. For example surfactants are used to stabilise emulsions and other compositions and are used in a whole range of cleaning applications including heavy industrial use, specialist surface cleaning, domestic use and in personal care compositions.

Several classes of surfactant compounds are known including anionic, cationic, amphoteric and non ionic surfactants. Different compounds having varying structures within these classes are known and are used for many different purposes.

Recently, suppliers and users of surfactants are becoming increasingly aware of the need for 'Green' surfactants. By 'Green' surfactants we mean to include surfactants which place less of a burden on the environment. In particular we mean surfactants which have a large proportion of the carbon content derived from renewable resources.

An aim of the present invention is to provide novel surfactant compounds which may be prepared from renewable sources of carbon. A further aim is to provide such surfactants which have low irritancy to skin and/or eyes. Yet another aim is to provide such surfactants for use in high foaming compositions.

According to a first aspect of the present invention there is provided a surfactant component comprising a compound of formula (I):

$$\underset{R^1}{\overset{O}{\|}}\underset{}{C}-R^2 \quad (I)$$

wherein $R^1$ is a $C_5$ to $C_{39}$ alkyl or alkenyl group and $R^2$ is a group of formula (a)

(a)

[structure showing furanone ring with WO—CH(OX)— substituent and YO, OZ groups]

wherein one of W, X, Y and Z is a covalent bond and the remaining groups are independently selected from H, M, $SO_3M$ and a further group of formula $R^1CO$ provided at least one of W, X, Y and Z is $SO_3M$; and each M is independently a hydrogen ion, an ammonium ion or a metal ion.

The surfactant component of the present invention may comprise a mixture of two or more compounds of formula (I).

$R^1$ is a $C_5$ to $C_{39}$ alkyl or alkenyl group. Preferably $R^1$ is a $C_5$ to $C_{35}$ alkyl or alkenyl group. Preferably $R^1$ is a $C_7$ to $C_{29}$ alkyl or alkenyl group, preferably $C_7$ to $C_{23}$, preferably $C_9$ to $C_{19}$, more preferably $C_9$ to $C_{17}$.

Preferably $R^1$ is an alkyl group.

$R^1$ may be a mixture of alkyl and/or alkenyl groups i.e. the surfactant component may include molecules of the compound of formula (I) in which different alkyl or alkenyl groups are present.

In some embodiments $R^1$ may be a mixture of alkyl and/or alkenyl groups derived from animal or plant triglycerides. Preferred are plant triglycerides, for example vegetable oils. $R^1COOH$ may represent a mixture of fatty acids derived from these triglycerides or oils.

In some embodiments $R^1CO$ is derived from a cocoyl group, for example a mixture of alkyl groups derived from coconut oil; palm oil or palm kernel oil.

$R^1$ may be a mixture of alkyl and/or alkenyl groups having 9 to 17, preferably 11 to 15, more preferably 11 to 13 carbon atoms.

In some especially preferred embodiments $R^1$ is $CH_3(CH_2)_{10}$ and the compound of formula (I) is prepared from lauric acid or a derivative thereof, for example lauroyl chloride.

The surfactant component of the present invention may comprise a mixture of compounds of formula (I). In some embodiments the compound of formula (I) may include two or three acyl groups of formula $R^1CO$. In such embodiments each group $R^1$ may be the same or different. However in preferred embodiments the surfactant component comprises compounds of formula (I) in which one of W, X, Y and Z is a covalent bond and the remaining groups are independently selected from H, M and $SO_3M$ and provided at least one of W, X, Y and Z is $SO_3M$.

Suitably the surfactant component of the present invention comprises a compound selected from one of the following esters:

(IIA)

[structure with $R^1CO$—O—CH2—CH(OX)— attached to furanone ring with YO, OZ groups]

(IIB)

[structure with WO—CH2—CH— attached to furanone ring with YO, OZ groups, and O—CO—$R^1$ substituent]

-continued

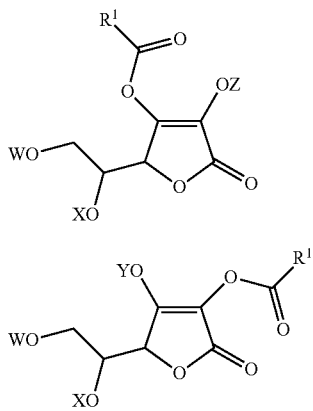

In the compound of formula (II A) each of X, Y and Z is independently selected from $R^1CO$, hydrogen, M and $SO_3M$; preferably each is selected from hydrogen, M and $SO_3M$ wherein at least one is $SO_3M$.

In the compound of formula (II B) each of W, Y and Z is independently selected from $R^1CO$, hydrogen, M and $SO_3M$; preferably each is selected from hydrogen, M and $SO_3M$ wherein at least one is $SO_3M$.

In the compound of formula (II C) each of W, X and Z is independently selected from $R^1CO$, hydrogen, M and $SO_3M$; preferably each is selected from hydrogen, M and $SO_3M$ wherein at least one is $SO_3M$.

In the compound of formula (II D) each of W, X and Y is independently selected from $R^1CO$, hydrogen, M and $SO_3M$; preferably each is selected from hydrogen, M and $SO_3M$ wherein at least one is $SO_3M$.

M is as later defined herein.

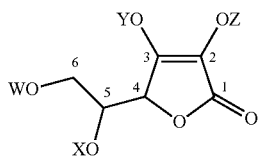

With reference to the numbering in the structure above the surfactant component of the present invention may be selected from 6 acyl ascorbic acid sulphate, 5 acyl ascorbic acid sulphate, 3 acyl ascorbic acid sulphate, 2 acyl ascorbic acid sulphate or derivatives thereof having further acyl groups and/or further sulphate groups or mixtures thereof.

The surfactant component of the present invention may comprise a compound of formula (I) selected from 6 acyl ascorbic acid 2 sulfate, 6 acyl ascorbic acid 3 sulfate, 6 acyl ascorbic acid 5 sulfate, 5 acyl ascorbic acid 2 sulfate, 5 acyl ascorbic acid 3 sulfate, 5 acyl ascorbic acid 6 sulfate, 3 acyl ascorbic acid 2 sulfate, 3 acyl ascorbic acid 6 sulfate, 3 acyl ascorbic acid 5 sulfate, 2 acyl ascorbic acid 3 sulfate, 2 acyl ascorbic acid 5 sulfate, 2 acyl ascorbic acid 6 sulfate or derivatives thereof having further acyl groups and/or further sulphate groups or mixtures thereof.

Preferably the surfactant component of the present invention comprises a compound selected from 6 acyl ascorbic acid 2 sulfate, 6 acyl ascorbic acid 3 sulfate, 6 acyl ascorbic acid 5 sulfate, 5 acyl ascorbic acid 2 sulfate, 5 acyl ascorbic acid 3 sulfate, 5 acyl ascorbic acid 6 sulfate, 3 acyl ascorbic acid 2 sulfate, 3 acyl ascorbic acid 6 sulfate, 3 acyl ascorbic acid 5 sulfate, 2 acyl ascorbic acid 3 sulfate, 2 acyl ascorbic acid 5 sulfate, 2 acyl ascorbic acid 6 sulfate or mixtures thereof.

In some preferred embodiments the surfactant component of the present invention comprises a compound of formula (I) selected from 6 acyl ascorbic acid 2 sulfate, 6 acyl ascorbic acid 3 sulfate, 3 acyl ascorbic acid 2 sulfate, 3 acyl ascorbic acid 6 sulfate, 2 acyl ascorbic acid 3 sulfate, 2 acyl ascorbic acid 6 sulfate or mixtures thereof.

Each of the sterocentres in compounds (IIA), (IIB), (IIC) and (IID) shown above may independently have an R or an S configuration.

In some preferred embodiments W is a covalent bond and the surfactant component of the present invention comprises a compound of formula (II A):

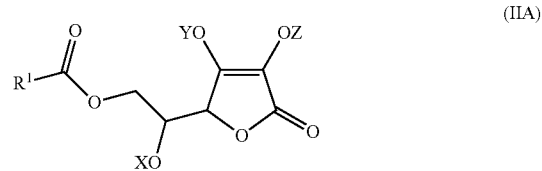

In some preferred embodiments in which Z is a covalent bond the surfactant component of the invention comprises a compound of formula (IID):

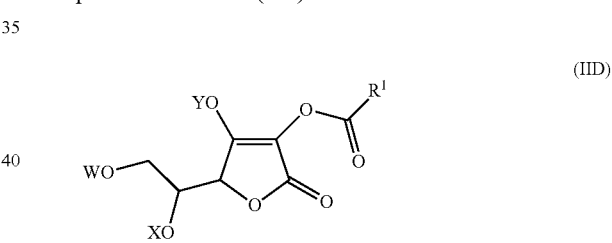

Thus the compound of formula (I) may be provided as any enantiomer or any diastereomer and may comprise a racemic mixture of enantiomers and/or a mixture of diastereomers.

In some preferred embodiments the compound has the formula:

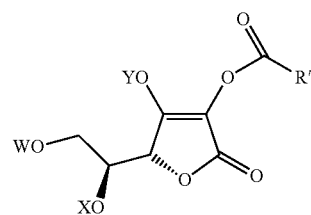

Each of W, X and Y may independently be H, M or $SO_3M$ wherein M is a hydrogen ion, an ammonium ion or a metal ion.

In some preferred embodiments the compound of the present invention has the formula:

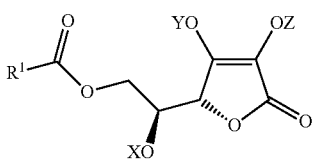

Each of X, Y and Z may independently be H, M or $SO_3M$ wherein M is a hydrogen ion, an ammonium ion or a metal ion.

The skilled person will appreciate that the group $SO_3M$ may be written as $SO_3^-M^+$.

In some embodiments M is a polyvalent cation and more than one anion is present.

When M is an ammonium cation this may be a substituted or unsubstituted ammonium ion.

Suitable substituted ammonium ions will be known to the person skilled in the art and include ions derived from primary, secondary and tertiary amines. Preferred substituted ammonium ions include those derived from mono, di and tri alkyl amines and mono, di or tri hydroxyalkyl amines. Those derived from mono or tri alkyl or hydroxyalkyl amines are especially suitable, for example the quaternary ammonium salt of monoethanolamine or triethanolamine.

Suitable metal ions include alkali metal ions, for example sodium and potassium, and alkaline earth metal ions, for example calcium and magnesium.

Preferably M is a hydrogen ion, a monovalent metallic cation, or an ammonium cation.

Most preferably M is an alkali metal ion or an ammonium ion. In especially preferred embodiments M is sodium, potassium or $NH_4^+$.

In some embodiments X is hydrogen, Y is hydrogen and Z is $SO_3M$.

In some embodiments X is hydrogen, Y is $SO_3M$ and Z is $SO_3M$.

In some embodiments X is $SO_3M$, Y is $SO_3M$ or, and Z is $SO_3M$.

In some embodiments X is hydrogen, Y is $SO_3M$ and Z is hydrogen.

In some embodiments X is $SO_3M$, Y is hydrogen and Z is $SO_3M$.

In some embodiments X is $SO_3M$ or, Y is $SO_3M$ or and Z is hydrogen.

In especially preferred embodiments X is $SO_3M$, Y is hydrogen and Z is hydrogen.

In some preferred embodiments the surfactant component of the present invention comprises a compound of formula (III):

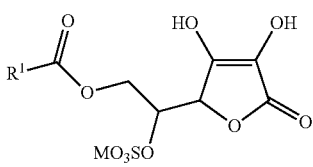

Suitably the compound has the formula:

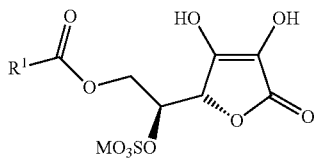

In some especially preferred embodiments the surfactant component of the present invention comprises a compound of formula (IV):

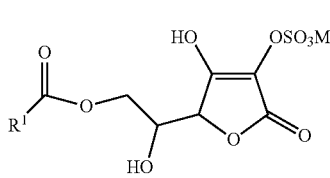

Most preferably the compound has the formula:

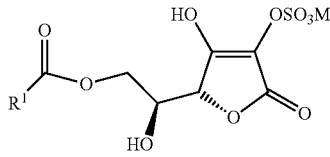

The first aspect of the present invention provides a surfactant component comprising a compound of formula (I). It may comprise a mixture of two or more compounds of formula (I).

Preferably the surfactant component of the first aspect comprises at least 5 wt % of one or more compounds of formula (I), preferably at least 10 wt %, more preferably at least 15 wt %, preferably at least 20 wt %, for example at least 25 wt % or at least 30 wt %.

In some embodiments the surfactant component of the first aspect may comprise more that 40 wt % of one or more compounds of formula (I), more than 50 wt %, more than 60 wt % or more than 70 wt %.

The surfactant component may in some embodiment comprise up to 100 wt % of one or more compounds of formula (I), for example up to 90 wt %.

Compounds of formula (I) may be considered to be ascorbic acid derived compounds. By ascorbic acid derived compounds we mean to include any compounds containing the core carbon structure found in ascorbic acid including the non-natural isomers. Thus ascorbic acid derived compounds may include ascorbic acid and compounds in which one, two, three or four of the hydroxyl groups of ascorbic acid have been reacted.

The compounds of formula (I) are ascorbic acid derivatives in which at least one hydroxyl group is sulphated and at least one hydroxyl group is substituted with an acyl group of formula $R^1CO$.

The surfactant component of the first aspect of the present invention may comprise minor amounts of ascorbic acid derived compounds not of formula (I). These typically include unreacted starting materials and byproducts, for example ascorbic acid, acylated ascorbic acid compounds which are not sulphated and sulphated ascorbic acid compounds which are not acylated.

Preferably compounds of formula (I) comprise the major proportion of all ascorbic acid derived compounds present in the surfactant component of the first aspect of the present invention. Preferably compounds of formula (I) comprise at least 50 wt % of all ascorbic acid derived compounds present in the surfactant component of the first aspect of the present invention, preferably at least 60 wt %, more preferably at least 70 wt %, preferably at least 80 wt %, for example at least 90 wt %.

The first aspect of the present invention suitably provides a surfactant component that can be easily incorporated into a formulated product, for example a cleaning composition or a personal care composition.

The surfactant component may consist essentially of one or more compounds of formula (I) and minor amounts of residual starting materials and/byproducts.

In some embodiments the surfactant component may further include a diluent or carrier. Suitable diluents and carriers will be known to the person skilled in the art and include, for example, water and water miscible solvents.

According to a second aspect of the present invention there is provided a method of preparing a compound of formula (I) the method comprising reacting an acid of formula $R^1COOH$ or a derivative thereof with a compound of formula $R^2H$ or a precursor thereof where $R^1$ and $R^2$ are as defined in relation to the first aspect.

The reaction may be carried out in a suitable solvent. It may involve heating and/or cooling the mixture, or it may be carried out under ambient conditions. Selection of appropriate reaction conditions is within the competence of the person skilled in the art.

$R^2H$ or a precursor thereof is suitably an alcohol. This is reacted with an acid of $R^1COOH$ or a derivative thereof to form an ester.

When the free acid is used a coupling agent may be used. These will be known to the person skilled in the art.

Other derivatives of acids useful in the preparation of esters and amides are well known to the skilled person. Preferred derivatives are acid chlorides.

Thus in some especially preferred embodiments the method of the second aspect of the present invention involves reacting an acid chloride of formula $R^1COCl$ with a compound of formula $R^2H$ or a precursor thereof.

Acid chlorides may be prepared from the acid by known techniques, for example by treatment with thionyl chloride or phosphorous trichloride.

Many acid chlorides are commercially available, for example lauroyl chloride, myristyl chloride and cocoyl chloride.

The method of the second aspect of the present invention may involve reacting an acid of formula $R^1COOH$ or a derivative thereof with a compound of formula:

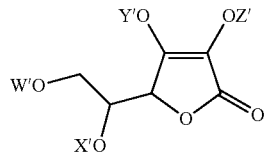

wherein each of W', X', Y' and Z' is independently selected from H, M and $SO_3M$ wherein at least one of W', X', Y' and Z' is hydrogen.

However in preferred embodiments, the acid or derivative thereof is reacted with a precursor alcohol of formula:

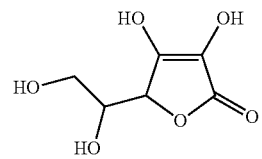

(X)

Methods of preparing esters of alcohols of formula (X) are well known. For example, fatty acid esters of ascorbic acid such as ascorbyl palmitate are taught in U.S. Pat. No. 2,368,435 and in "Synthesis of 6-fatty acid esters of L ascorbic acid (JAOCS 1977, Vol 54, 8, 308-312). In this latter reference, separate methods of preparing the ascorbyl 6 palmitate and the ascorbyl 2 palmitate are described.

The resulting ester is then subsequently reacted with a sulphating agent.

Thus in the method of the present invention an acid of formula $R^1COOH$ or a derivative thereof may be reacted with ascorbic acid.

The ester formed may be reacted with from 1 to 3 molar equivalents of a sulfating agent.

Preferably it is reacted with approximately 1 molar equivalent of sulfating agent.

Suitable sulfating agents and methods will be known to the person skilled in the art.

Preferred sulfating agents include sulphur trioxide, chlorosulfuric acid and oleum.

In the method of the second aspect the acid of formula $R^1COOH$ or a derivative thereof and the alcohol of formula $R^2H$ are suitably reacted in a molar ratio of from 2:1 to 1:2, preferably from 1.5:1 to 1:1.5, suitably from 1.2:1 to 1:1.2.

Suitable reaction conditions will be known to the person skilled in the art.

In some preferred embodiments the compound of formula $R^1COOH$ and the compound of formula $R^2H$ are obtained from natural sources. Thus the present invention may provide surfactants prepared from renewable sources. However the invention is not limited in this way and surfactant compounds prepared from other non-renewable sources are also within the scope of the invention.

Specific compounds formula (I) may find particular utility in certain types of application. For example, the HLB value of the compounds of formula (I) may vary depending, for example, the chain length of the $R^1$ group, the selected $R^2$ group, the nature of the anion(s), the presence and number of sulphate groups or phosphate groups etc.

Selecting appropriate compounds for a particular purpose is within the competence of the person skilled in the art.

In some preferred embodiments, compounds of the present invention may be particularly useful as detersive surfactants for example in cleaning applications or personal care applications. In other preferred embodiments compounds of the present invention may be particularly useful as emulsifiers.

According to the third aspect of the present invention there is provided a composition comprising a compound of formula (I).

The composition of the third aspect may comprise a diluent or carrier. It may comprise optional further components.

In some embodiments the composition of the third aspect may be a detersive surfactant composition, for example a cleaning composition or a personal care composition, When the composition of the third aspect is a liquid it may be a solution or an emulsion.

The composition of the third aspect of the present invention may be a cleaning composition or an emulsion.

In some embodiments the composition of the third aspect may be a laundry composition, an automatic dishwashing composition, a hand-dishwashing composition, a hard surface cleaner, a personal care composition or an animal hygiene composition.

In some embodiments the composition of the third aspect may be an oilfield production chemical composition.

The composition of the third aspect may be an antioxidant composition, a food additive, a health supplement or a medicinal composition.

In some embodiments the composition of the third aspect of the present invention is a laundry composition. The laundry composition may be provided in the form of a liquid, powder, granulate, gel or paste. In some embodiments the composition may be provided in unit dose form, for example in the form of a compressed tablet or an encapsulated liquid or gel.

Laundry compositions of the present invention may comprise any ingredient commonly used in such compositions. These will be known to the person skilled in the art and typical components vary depending on the form of the composition.

Suitably the laundry compositions comprise one or more compounds of formula (I), one or more further surfactants and one or more builders.

The laundry compositions may also comprise one or more further ingredients selected from chelating agents, bleaching agents, bleach activators, pigments, dyes, fragrances, enzymes, biocides, preservatives and pH adjusting agents.

In some embodiments the composition of the third aspect of the present invention is an automatic dishwashing composition. This may be provided in the form of a liquid, powder, granulate, gel or paste. Solid compositions are preferred.

The compositions may be provided in unit dose form, for example as a compressed tablet.

Automatic dishwashing compositions of the present invention may comprise any ingredient commonly used in such compositions. These will be known to the person skilled in the art.

Suitably the automatic dishwashing compositions of the present invention comprise one or more compounds of formula (I), one or more further surfactants and one or more builders.

The automatic dishwashing compositions may further comprise one or more further components selected from chelating agents, enzymes, bleaching agents, bleach activators, biocides, rinse aids, dyes, pigments, fragrances, glass care agents and pH adjusting agents.

Suitable builders for use in the laundry and automatic dishwashing compositions of the present invention include phosphates, silicates and zeolites. Silicates and zeolites are preferred.

In some embodiments, the composition of the present invention is a hand dishwashing composition. This is suitably provided as a liquid which may be of a concentrated form. Compositions of this type are known to the person skilled in the art.

Hand dishwashing compositions of the present invention may comprise any ingredient commonly used in such compositions. These will be known to the person skilled in the art.

Suitably the hand-dishwashing compositions of the present invention comprise one or more compounds of formula (I), water and one or more additional surfactants.

The hand dishwashing compositions may comprise one or more additional components selected from chelating agents, dyes, pigments, fragrances, biocides and preservatives.

In some embodiments the composition of the third aspect of the present invention is a hard surface cleaner. This may be provided in the form of a powder or a granulate, gel, paste or liquid. It may be provided neat, in unit dose form, or in a ready to apply format. The hard surface composition may be impregnated on a wipe or be provided in a spray dispenser.

The hard surface cleaners of the present invention may comprise any ingredients commonly used in such compositions. These will be known to the person skilled in the art.

Preferably the hard surface cleaner of the present invention comprises one or more compounds of formula (I), one or more additional surfactants and water.

The hard surface cleaner compositions may further comprise one or more additional components selected from chelating agents, bleaching agents, bleaching activators, dyes, pigments, fragrances, biocides, pH adjusting agents and preservatives.

Suitable bleaching agents which may be used in the laundry, automatic dishwashing and hard surface cleaning compositions of the present invention include peroxide based compounds especially hydrogen peroxide, chlorine bleaches and perborate compounds.

Bleach activators and catalysts may also be present in such compositions.

In some preferred embodiments the composition of the third aspect is an oilfield production chemical composition.

Oilfield production chemical compositions of the present invention may give wetting, emulsification, foaming, lubricity or dispersion properties. The oilfield production chemical composition typically may be used in down hole and/or top side facilities. The oilfield production chemical composition may be used in lifting fluids, drilling fluids, cements, stimulation, enhanced oil recovery, completion fluids and workover fluids.

Oilfield production chemical compositions of the present invention may comprise any ingredient commonly used in such compositions. These will be known to those skilled in the art and include further surfactants, rheology modifiers, solvents, corrosion inhibitors, flocculants, drag reducers, biocides, scale inhibitors, chelants or scavengers.

In some preferred embodiments the composition of the third aspect is a personal care composition. Suitable personal care compositions include cleansing compositions and emulsions.

The personal care composition may be a hair care product, oral care product, skin care products or body care product.

The personal care compositions of the present invention may be in the form of a solid, liquid, gel, paste or foam.

The personal care composition may be a shampoo, a shower gel, toothpaste, moisturiser, shaving foam or gel, hand wash, body wash, bath foam, bubble bath, soap bar, liquid soap, toilet bar, facial cleaner, skin cleanser, make-up remover etc.

Suitable personal care emulsions include conditioners, moisturisers and sunscreens.

In some embodiments the composition is a hair care composition.

In some embodiments the composition is a skin care composition.

Suitably the composition is a mild shampoo composition or a mild cleansing composition.

By mild composition we mean to refer to compositions which have low irritancy.

Suitably the composition of the third aspect of the present invention may be a baby product; for example a baby shampoo or a baby bubble bath.

Suitably the composition of the third aspect may be a facial cleansing composition.

The composition of the third aspect of the present invention may be an animal hygiene composition. Suitable animal hygiene compositions include shampoos, grooming aids, conditioners, wash compositions, bath compositions, toothpaste etc. Preferred aspects of animal hygiene compositions are the same as for personal care compositions.

Personal care or animal care compositions of the present invention may be provided in any suitable form. For example they may be provided as a powder or as a gel, paste or cream.

In some embodiments the composition is provided in solid form. For example it may be provided in the form of a facial cleansing bar. Such bars have the general form and appearance of soap bars but typically contain one or more synthetic surfactant compounds, for example those known to be milder than traditional soap.

In some embodiments the composition may be impregnated on a wipe, for example to provide a facial cleansing wipe.

Preferably the composition is a liquid composition.

The composition of the third aspect is preferably an aqueous composition. Other water miscible solvents may be included, for example mono or polyhydric alcohols, such as glycerol. Preferably water accounts for at least 50 wt % of all solvents present in the composition, preferably at least 70 wt %, suitably at least 80 wt %, preferably at least 90 wt %, for example at least 95 wt %.

The composition of the third aspect preferably comprises at least 0.001 wt % of the compound of formula (I), preferably at least 0.01 wt %, more preferably at least 0.05 wt %, preferably at least 0.1 wt %, suitably at least 0.25 wt %, preferably at least 0.5 wt %, for example at least 0.6 wt %, at least 0.7 wt % or at least 0.8 wt %.

The compound of the formula (I) may be present in an amount of up to 99 wt %, suitably up to 60 wt %, preferably up to 50 wt %, suitably up to 40 wt %, preferably up to 35 wt %, more preferably up to 30 wt %, for example up to 25 wt %, up to 23 wt % or up to 22 wt %.

In some preferred embodiments in which the composition is a personal care composition the compound of formula (I) is present in an amount of from 0.1 to 20 wt %, preferably from 0.5 to 10 wt %.

The compositions of the present invention may comprise a mixture of two or more compounds of formula (I). The above amounts refer to the total of all such compounds present in the composition.

In some embodiments the compositions of the third aspect of the present invention may comprise a surfactant component of the first aspect. In such embodiments the above amounts of the compound of formula (I) present in the composition refer to the amount of active compounds of formula (I) and ignore any unreacted starting material, byproduct, diluent or carrier that may be present.

The compositions of the third aspect of the present invention preferably comprise one or more additional surfactants.

Suitable surfactants include anionic surfactants, non-ionic surfactants, cationic surfactants, amphoteric surfactants, and mixtures thereof.

Suitable anionic surfactants include salts of alkyl sulfates, alkyl ether sulfates, fatty acids, carboxylates, alkyl sulfonates, aryl sulfonates, alkyl benzene sulphonates, isethionates, alkyl phosphates, sulfosuccinates, taurates, sarcosinates, sulfoacetates, lactates, acyl amino acids and phosphonates, Suitable non-ionic surfactants include fatty alcohols, alkoxylated alcohols, alkoxylated phenols, alkyl amine oxides, alkyl phosphine oxides, alkyl sulfoxides, sorbitan and sucrose esters, alkylpolyglucosides and alkoxylated alkylpolyglucosides, Suitable cationic surfactants include fatty amine derivatives, phosphonium quaternary ions, ammonium quaternary ions and sulphonium ions.

Suitable amphoteric surfactants include alkyl betaines, alkyl sultaines and amphoacetates.

Laundry, automatic dishwashing and hard surface compositions of the present invention preferably comprise anionic surfactants, for example alkyl sulfates and alkyl ether sulfates.

In some embodiments the compounds of the present invention have desirable foaming properties, for example when used in personal care, animal care, laundry or hand dishwashing compositions. By this we mean that a composition comprising the compound when used as a cleaning or cleansing composition produces a tight long lasting foam and has reasonable foam volume.

A suitable method for measuring foam volume is the cylinder shake method. In the cylinder shake method 50 ml of 1% active surfactant solution is put into a 250 ml graduated stoppered measuring cylinder. The cylinder is shaken for a set number of times and then placed at ambient temperature. The total volume of the foam generated is recorded.

Preferably the personal care, animal care, laundry and hand dishwashing compositions of the present invention are low irritancy compositions. Suitably the personal care, animal care, laundry and hand dishwashing compositions of the present invention have low skin irritancy.

Skin irritancy may be measured by any suitable method and such methods will be known to the person skilled in the art. One suitable method by which skin irritancy can be measured is the Zein test.

The purpose of the Zein Solubility Test Method is to investigate the irritation potential (harshness) of a surfactant or product. In the test, Zein, a yellow corn protein that is similar to keratin present in the skin and hair, is denatured (solubilized) by the test irritant. Predicted irritation potential is determined by the amount of Zein solubilized.

The test method involves mixing a known amount of test composition with a defined mass of the Zein protein. The solution is allowed to mix for a set period of time, whilst checking to ensure that there is enough remaining solid Zein in the mixture. If most of the Zein dissolves, then more Zein is added. The resulting solution/undissolved Zein is then filtered and dried. The mass of residual Zein is determined gravimetrically. The more irritating the test composition, the higher the level of Zein dissolved.

Preferably the personal care, animal care, laundry and hand dishwashing compositions of the present invention pass the Zein test.

Preferably the personal care and animal care compositions of the present invention have low ocular irritancy.

Ocular irritation can be measured by any suitable method and such methods will be known to the person skilled in the art. A standard method known since 1944 is the Draize Eye Irritancy Test. This is a long established test which involves delivery of a material into the conjunctival sac of one eye of a rabbit. However this test is now used less often as it is often considered cruel and alternative in vitro tests have been developed. One suitable method is the "EpiOcular" (®) of MatTek. This corneal model consists of normal, human-derived epidermal keatinocytes which have been cultured to form a stratified, squamous epithelium similar to that found in the cornea. The epidermal cells, which are cultured on specially prepared cell culture inserts using serum free medium, differentiate to form a multilayered structure which closely parallels the corneal epithelium. The system is said to provide a predictive, morphologically relevant in vitro means to assess ocular irritancy. The results from the Epi-Oculuar (®) test allow a composition to be classified as severely irritating, moderately irritating, mildly irritating or minimally or non-irritating.

Suitably the low irritancy cleansing formulation of the present invention would be classified as mildly irritating, minimally irritating or non-irritating on the EpiOcular (®) test. Preferably it would be classified as non-irritating or minimally irritating.

Details of the EpiOcular (®) test can be found in the paper entitled "Evaluation of the EpiOcular™ Tissue Model as an Alternative to the Draize Eye Irritation Test"; M. Stern, M. Klausner, R. Alvarado, K. Renskers, M. Dickens; *Toxicology in Vitro*, Volume 12, Issue 4, August 1998, Pages 455-461.

As mentioned above a number of in vitro eye irritancy tests are available. Many of these tests allow the results to be correlated to provide an equivalent score on the Draize test. In order to allow a correlation to be made it is often necessary to carefully select appropriate conditions, especially concentration. However the performance of such a test would be well within the competence of the skilled person.

The composition of the present invention would preferably be such that when testing using in vitro tests of this type it would provide a score equivalent to mild or non-irritating on the Draize Test.

As mentioned above, the compositions of the third aspect may comprise a mixture of compounds of formula (I).

The composition may comprise one or more further surfactants. These may be selected from anionic, cationic, non-ionic and amphoteric surfactants.

Suitable further surfactant compounds for use in the compositions of the present invention depend on the desired end use of the composition. However selection of an appropriate surfactant or mixture of surfactants will be within the competence of the skilled person.

Suitable surfactants for use in laundry compositions of the present invention include anionic surfactants, non-ionic surfactants, cationic surfactants, zwitterionic surfactants, amphoteric surfactants and mixtures thereof.

Suitable anionic surfactants for use in laundry compositions of the present invention typically comprise one or more moieties selected from the group consisting of carbonate, phosphate, phosphonate, sulphate, sulphonate, carboxylate and mixtures thereof. The anionic surfactant may be one or mixtures of more than one of alkyl or alkenyl sulphates and alkyl sulphonates.

Suitable anionic surfactants incorporated alone or in mixtures for use in the laundry compositions of the present invention include C8-18 alkyl sulphates and/or C8-18 alkyl sulphonates optionally condensed with from 1 to 9 moles of C1-4 alkylene oxide per mole of C8-18 alkyl sulphate and/or C8-18 alkyl sulphonate. The alkyl chain of the C8-18 alkyl sulphates and/or C8-18 alkyl sulphonates may be linear or branched, preferred branched alkyl chains comprise one or more branched moieties that are C1-6 alkyl groups.

Preferred anionic surfactants for use in laundry compositions of the present invention are alkyl or alkenyl benzene sulphates and/or alkyl or alkenyl benzene sulphonates. The alkyl chain of the C8-18 alkyl benzene sulphates and/or C8-18 alkyl benzene sulphonates may be linear or branched, preferred branched alkyl chains comprise one or more branched moieties that are C1-6 alkyl groups.

Other preferred anionic surfactants for use in laundry compositions of the present invention are selected from the group consisting of: C8-18 alkenyl sulphates, C8-18 alkenyl sulphonates, C8-18 alkenyl benzene sulphates, C8-18 alkenyl benzene sulphonates, C8-18 alkyl di-methyl benzene sulphate, C8-18 alkyl di-methyl benzene sulphonate, fatty acid ester sulphonates, di-alkyl sulphosuccinates, and combinations thereof.

Other useful anionic surfactants for use in laundry compositions of the present invention include the esters of alpha-sulfonated fatty acids, typically containing from 6 to 20 carbon atoms in the fatty acid group and from 1 to 10 carbon atoms in the ester group; 2-acyloxyalkane-1-sulfonic acid and salts thereof, typically containing from about 2 to 9 carbon atoms in the acyl group and from about 9 to 23 carbon atoms in the alkane moiety; alpha-olefin sulfonates (AOS), typically containing from about 12 to 24 carbon atoms; and beta-alkoxy alkane sulfonates, typically containing from about 1 to 3 carbon atoms in the alkyl group and from about 8 to 20 carbon atoms in the alkane moiety. Also useful are the sulphonation products of fatty acid esters containing an alkyl group typically with from 10 to 20 carbon atoms. Preferred are C1-4, most preferably methyl ester sulphonates. Preferred are C16-18 methyl ester sulphonates (MES).

The anionic surfactants may be present in the salt form. For example, the anionic surfactant(s) may be an alkali metal salt of any of the above. Preferred alkali metals are sodium, potassium and mixtures thereof Suitable non-ionic surfactants for use in laundry compositions of the present invention may be selected from the group consisting of: alkyl alkoxylates, alkyl phenol alkoxylates, C12-C18 alcohol and C6-C12 alkyl phenol condensates with ethylene oxide/propylene oxide block polymers; C14-C22 mid-chain branched alcohols, C14-C22 mid-chain branched alkyl alkoxylate, alkylpolysaccharides, specifically alkylpolyglycosides, polyhydroxy fatty acid amides, ether capped poly(oxyalkylated) alcohol surfactants and mixtures thereof.

Suitable cationic detersive surfactants for use in laundry compositions of the present invention include alkyl pyridinium compounds, alkyl quaternary ammonium compounds, alkyl quaternary phosphonium compounds, and alkyl ternary sulphonium compounds. The cationic detersive surfactant can be selected from the group consisting of: alkoxylate quaternary ammonium (AQA) surfactants, dimethyl hydroxyethyl quaternary ammonium, polyamine cationic surfactants, cationic ester surfactants, amino surfactants, specifically amido propyldimethyl amine; and mixtures thereof.

Preferred cationic detersive surfactants for use in laundry compositions of the present invention are quaternary ammonium compounds having the general formula:

$$(R)(R^1)(R^2)(R^3)N^+X^-$$

wherein, R is a linear or branched, substituted or unsubstituted C6-18 alkyl or alkenyl moiety, $R^1$ and $R^2$ are independently selected from methyl or ethyl moieties, $R^3$ is a hydroxyl, hydroxymethyl or a hydroxyethyl moiety, X is an anion which provides charge neutrality.

Alkyl benzene sulphonates are preferred anionic surfactants for use in laundry compositions of the present invention.

Suitable surfactants for use in automatic dishwashing compositions of the present invention include anionic surfactants, non-ionic surfactants, cationic surfactants, zwitterionic surfactants, amphoteric surfactants and mixtures thereof.

In addition to the ingredients previously described, the automatic dishwashing compositions of the present invention may comprise further active washing or cleaning substances, preferably from the group of surfactants, enzymes, organic solvents, glass corrosion inhibitors, corrosion inhibitors, scents and perfume carriers.

All non-ionic surfactants known to the person skilled in the art can be used in principle as non-ionic surfactants in the automatic dishwashing compositions of the present invention. Alkyl glycosides of the general formula RO(G)x for example are suitable as non-ionic surfactants, in which R denotes a primary straight-chain or methyl-branched aliphatic residue, in particular one methyl-branched in the 2-position, having 8 to 22, preferably 12 to 18 C atoms, and G is the symbol which stands for a glycose unit having 5 or 6 C atoms, preferably for glucose. The degree of oligomerization x, which indicates the distribution of monoglycosides and oligoglycosides, is any number between 1 and 10; x is preferably between 1.2 and 1.4.

Non-ionic surfactants of the amine oxide type, for example N-cocoalkyl-N,N-dimethyl amine oxide and N-tallow alkyl-N,N-dihydroxyethyl amine oxide, and of the fatty acid alkanol amide type can also be suitable for use in automatic dishwashing compositions of the present invention. The amount of these non-ionic surfactants is preferably no more than that of the ethoxylated fatty alcohols, in particular no more than half that.

Another class of non-ionic surfactants which may be used in automatic dishwashing compositions of the present invention either as the only non-ionic surfactant or in combination with other non-ionic surfactants, are alkoxylated, preferably ethoxylated or ethoxylated and propoxylated, fatty acid alkyl esters, preferably having 1 to 4 carbon atoms in the alkyl chain.

Slightly foaming non-ionic surfactants are preferred surfactants for use in the automatic dishwashing compositions of the present invention. Washing or cleaning agents, in particular cleaning agents for automatic dishwashing, contain to particular advantage non-ionic surfactants from the group of alkoxylated alcohols.

Alkoxylated, advantageously ethoxylated, in particular primary alcohols having preferably 8 to 18 C atoms and on average 1 to 12 mol of ethylene oxide (EO) per mol of alcohol are preferably used as non-ionic surfactants in the automatic dishwashing compositions of the present invention, in which the alcohol residue can be linear or preferably methyl-branched in the 2-position or can contain linear and methyl-branched residues in the mixture, such as are conventionally present in oxoalcohol residues.

In preferred embodiments in which the composition of the third aspect is a personal care composition, one or more further cosmetically approved surfactants may be included in the composition. Such surfactants are known to the person skilled in the art. Examples of such surfactants may be found in for example, the CTFA Cosmetic Ingredient Handbook, Second Edition, The Cosmetic, Toiletries, and Fragrance Association, Inc. 1988, 1992.

Such surfactants are known to the person skilled in the art and may be selected from anionic surfactants, cationic surfactants, amphoteric surfactants, non-ionic surfactants and mixtures thereof.

Suitable cationic surfactants for use in the personal care compositions of the present invention include those based on fatty amine derivates or phosphonium quaternary ions, and quaternary ammonium compounds. Suitable cationic surfactants for use herein include tertiary amine salts and tetra alkyl ammonium salts such as tetra alkyl ammonium halides and tetra alkyl ammonium methyl sulfates.

Preferred cationic surfactants for use herein include tertiary amine salts, mono alkyl trimethyl ammonium chloride, mono alkyl trimethyl ammonium methyl sulphate, dialkyl dimethyl ammonium chloride, dialkyl dimethyl ammonium methyl sulphate, trialkyl methyl ammonium chloride, trialkyl methyl ammonium methyl sulphate, mono alkyl triethyl ammonium chloride, mono alkyl triethyl ammonium methyl sulphate, dialkyl diethyl ammonium chloride, dialkyl diethyl ammonium methyl sulphate, trialkyl ethyl ammonium chloride and trialkyl ethyl ammonium methyl sulfate.

Suitable anionic surfactants for use in the personal care compositions of the present invention include salts of: fatty acids; alkoxylated carboxylic acids; ester carboxylates; ethoxylated ester carboxylates; mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; isethionates, alkyl isethionates, acyl isethionates, acyl alkyl isethionates, alkyl glyceryl ether sulfonates; alpha-olefin sulfonates; alkyl phosphates; sulfonates of alkylphenolpolyglycol ethers; alkyl sulfopolycarboxylic acid esters; alkyl sulfosuccinates; alkyl ether sulfosuccinates; taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids, lipoamino acids and acyl substituted amino acids, for example acyl glycinates and acyl glutamates. Particularly exemplary salts of the above, where applicable, are the sodium, potassium, ammonium, magnesium and triethanolamine salts.

Preferred anionic surfactants include alkyl or alkenyl sulfates, alkyl or alkenyl ether sulfates, alkyl glyceryl ether sulfates, taurates, acyl taurates, (alkyl) isethionates (alkyl) acyl isethionates, acyl substituted amino acids, sarcosinates, sulfosuccinates, sulfosuccinamates, sulphoacetates, monoalkyl phosphate esters, di-alkyl phosphate esters, monoalkyl ether phosphate esters, di-alkyl ether phosphate esters, alpha-olefin sulfonates, acyl lactates, alkyl ether carboxylates, glyceryl ether carboxylates.

Particularly preferred anionic surfactants for use herein include alkyl or alkenyl sulfates, alkyl or alkenyl ether sulfates, taurates, isethionates, acyl substituted amino acids, sarcosinates, and sulfosuccinates.

Illustrative examples of preferred anionic surfactants include sodium lauryl sulphate, sodium lauryl ether sulfate, sodium lauroyl methyl taurate, sodium methyl cocoyl taurate, sodium methyl oleoyl taurate, sodium cocoyl isethionate, sodium lauroyl isethionate, sodium lauroyl methyl isethionate, sodium lauroyl glycinate, sodium cocoyl glycinate, sodium lauryl sarcosinate, and disodium oleamido mipa sulfosuccinate.

Suitable alkyl or alkenyl sulfates and ether sulfates are compounds of formula:

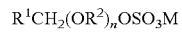

wherein $R^1$ and P are as defined in relation to the compound of formula (I);

$R^2$ is an alkylene group having 1 to 4 carbon atoms and n is from 0 to 12.

$R^2$ is preferably a propylene or especially an ethylene moiety. Preferably n is from 0 to 6, preferably from 0 to 4, for example from 0 to 2. In some embodiments n is 0. In some embodiments n is 2.

Suitable non-ionic surfactants for use in the personal care compositions of the present invention include reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl (C6-C22) phenol-ethylene oxide condensates, the condensation products of aliphatic (C8-C18) primary or secondary linear or branched alcohols with ethylene oxide, and products made by condensation of ethylene oxide with the reaction products of propylene oxide and ethylenediamine); alkyl tertiary amine oxides, alkyl tertiary phosphine oxides and dialkyl sulphoxides; alkyl amine oxides, alkyl amido amine oxides; alkyl tertiary phosphine oxides; alkoxyl alkyl amines; sorbitan; sorbitan esters; sorbitan ester alkoxylates; glycerol ester alkoxylates; sucrose esters; sugar amides, such as polysaccharide amides; lactobionamides; and alkyl polysaccharide nonionic surfactants, for example alkylpolyglycosides and alkoxylated alkylpolyglycosides.

Preferred non-ionic surfactants include alkoxylated fatty alcohols, alkoxylated fatty acids, alkoxylated glycerol esters and alkoxylated sugar esters, for example alkoxylated sorbitan esters, especially ethoxylated species and especially those including lauryl, cetylstearyl, stearyl, cetyl and oleocetyl residues; alkyl polyglucosides; alkoxylated alkyl polyglucosides; alkanolamides and amineoxides. Some preferred nonionic surfactants include ethoxylated sorbitan laurates.

Suitable amphoteric surfactants for use in the personal care compositions of the present invention include those based on fatty nitrogen derivates and those based on betaines. Suitable amphoteric or zwitterionic surfactants may be selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetate.

Amphoteric or zwitterionic surfactants for use in the compositions of the present invention may include those which have an alkyl or alkenyl group of 5 to 39 carbon atoms and comply with an overall structural formula:

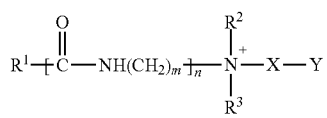

wherein $R^1$ are as defined in relation to the compound of formula (I) $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Preferably the personal care compositions of the present invention include one or more surfactants known to be mildly irritating to the skin and/or eyes.

In some embodiments the personal care composition includes an alkoxylated non-ionic species.

Suitable non-ionic surface-active agents may be selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenol-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine); and sorbitan ester alkoxylates. Preferred non-ionic surfactants include alkoxylated fatty alcohols, alkoxylated fatty acids, alkoxylated glycerol esters and alkoxylated sorbitan esters, especially ethoxylated species and especially those including lauryl, cetylstearyl, stearyl, cetyl and oleocetyl residues.

Preferably the non-ionic surfactant comprises at least 20 alkylene oxide residues, preferably at least 40, for example at least 60.

Preferred non-ionic surfactants for use as component (c) are those which are formed by the reaction of a compound including a hydrophobic group and ethylene oxide.

One suitable class of non-ionic surfactants are polyethylene sorbitan fatty acid esters with the esterifying fatty acid being selected from the group consisting of $C_{12}$-$C_{18}$ fatty acids wherein an average of about 1 or 3 of said acids are esterified per polyoxyethylene sorbitan molecule. One preferred non-ionic surfactant is a mixture of laurate esters of sorbitol and sorbitol anhydrides (sorbitan) consisting predominantly of the mono-ester condensed with about 20 moles of ethylene oxide. This surfactant is designated in the CTFA dictionary as Polysorbate 20 and is also known in the art as polyoxyethylene (20) sorbitan monolaurate and is available from several commercial sources.

Another suitable example of a polyoxyethylene alkyl ester is the CTFA designated Polysorbate 80 which is a mixture of oleate esters of sorbitol and sorbitol anhydrides, condensed with approximately 80 moles of ethylene oxide.

The personal care compositions of the present invention may comprise an amphoteric surfactant. This may be selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetates.

Surfactants suitable for use in the personal care compositions of the present invention may include alkyl betaines of formula:

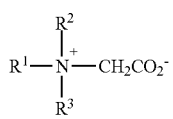

and alkyl amido betaines of formula:

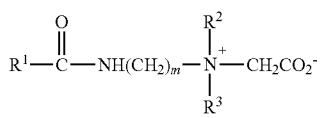

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Suitable surfactants include sultaines (or sulphobetaines) of formula:

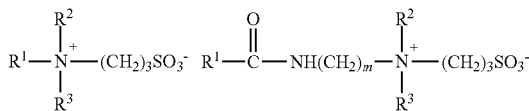

where m is 2 or 3, or variants of these in which —(CH$_2$)$_3$SO$_3^-$ is replaced by

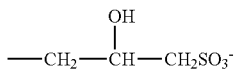

where R$^1$, R$^2$ and R$^3$ in these formulae are as defined previously.

Suitable surfactants include amphoacetates and diamphoacetates. Amphoacetates generally conform to the following formula:

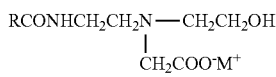

Diamphoacetates generally conform to the following formula:

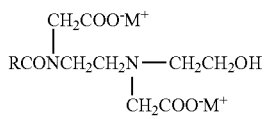

where R is an aliphatic group of 8 to 22 carbon atoms and M is a cation such as sodium, potassium, ammonium, or substituted ammonium.

Suitable acetate-based amphoteric surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium caprylamphodiacete; disodium lauroamphoacetate; sodium lauroamphoacetate and disodium wheatgermamphodiacetate.

Suitable betaine surfactants include alkylamido betaine; alkyl betaine, C$_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, C$_8$ amido betaine; C$_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N, N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocoamidopropyl hydroxy sultaine; undecylenamidopropyl betaine; cocoamidosulfobetaine; alkyl amido betaine; C$_{12/18}$ alkyl amido propyl dimethyl amine betaine; lauryldimethyl betaine; ricinol amidobetaine; tallow aminobetaine.

Suitable glycinate-based amphoteric surfactants include cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N—C$_{10/12}$ fatty acid amidoethyl-N-(2-hydroxyethyl)-glycinate; N—C$_{12/18}$-fatty acid amidoethyl-N-(2-hydroxyethyl)-glycinate; di hydroxyethyl tallow glycinate.

Preferred acetate-based amphoteric surfactants for use in the personal care compositions of the present invention include sodium lauroamphoacetate, disodium lauroamphoacetate and mixtures thereof.

Preferred betaine surfactants for use in the personal care compositions of the present invention include cocoamidopropyl betaine.

Preferred sultaine surfactants for use in the personal care compositions of the present invention include cocoamidopropylhydroxy sultaine.

In some embodiments the personal care compositions of the present invention include one or more acyl substituted amino acid surfactants. Suitable amino acids or amino acid salts from which such surfactants may be derived include any α-amino acids or β-amino acids which may be acylated to form N-acylamino acids or salts. Such amino acids are known to the skilled person.

Preferred amino acids are glutamic acid, sarcosine, aspartic acid, alanine, valine, leucine, isoleucine, proline, hydroxyproline, glycine, serine, cysteine, cystine, threonine, histidine and salts thereof and, more particularly, glutamic acid, sarcosine, aspartic acid, glycine, lysine and salts thereof. Glutamic acid, sarcosine, aspartic acid, glycine, methionine and lysine are particularly preferred. The amino acids may be used in optically pure form or as racemic mixtures.

The acyl group of the N-acylamino acids or salts may be represented by R$^1$COO where R$^1$ is as defined in relation to the compound of formula (I)

In some embodiments, preferred acyl substituted amino acid surfactants may be represented by the formula

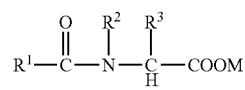

wherein R$^1$ and M are as defined in relation to the compound of formula (I)

R$^2$ is H or methyl, R$^3$ is H or —(CH$_2$)$_n$COOM, wherein n is from =0 to 2.

Suitable glutamate surfactants include compounds of formula:

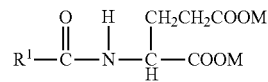

wherein $R^1$ and M are as defined in relation to the compound of formula (I).

Examples of suitable glutamate surfactants include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof.

Preferred glutamate surfactants include disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, sodium myristoyl glutamate and mixtures thereof. More preferred include disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, sodium lauroyl glutamate and mixtures thereof.

Suitable α-alanine or β-alanine surfactants include compounds having the general formula:

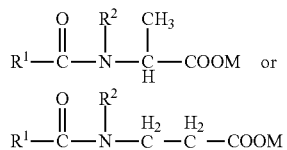

wherein $R^1$ and M are as defined in relation to the compound of formula (I) and $R^2$ is H or methyl.

Examples of suitable alanine surfactants include cocoyl methyl β-alanine, lauroyl β-alanine, lauroyl methyl β-alanine, myristoyl β-alanine, potassium lauroyl methyl β-alaninate, sodium cocoyl alaninate, sodium cocoyl methyl β-alaninate and sodium myristoyl methyl β-alaninate and mixtures thereof.

Suitable glycinate surfactants include compounds having the general formula:

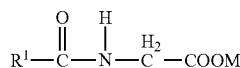

wherein $R^1$ and M are as defined in relation to the compound of formula (I)

Examples of suitable glycinate surfactants include palmitoyl glycine, sodium lauroyl glycinate, sodium cocoyl glycinate, sodium myristoyl glycinate, potassium lauroyl glycinate, and potassium cocoyl glycinate and mixtures thereof.

Suitable sarcosinate surfactants include compounds having the general formula:

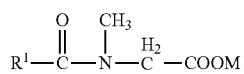

wherein $R^1$ and M are as defined in relation to the compound of formula (I).

Examples of suitable sarcosinate surfactants include potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred compounds include potassium lauroyl sarcosinate, potassium cocoyl sarcosinate, sodium cocoyl sarcosinate, sodium lauroyl sarcosinate and mixtures thereof. More preferred compounds include sodium cocoyl sarcosinate, and sodium lauroyl sarcosinate and mixtures thereof.

Suitable aspartate surfactants include compounds having the general formula:

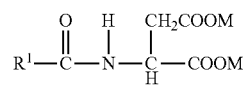

wherein $R^1$ and M are as defined in relation to the compound of formula (I)

Examples of suitable aspartate surfactants include sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate and mixtures thereof. Preferred compounds include sodium lauroyl aspartate, sodium myristoyl aspartate, sodium cocoyl aspartate, sodium caproyl aspartate and mixtures thereof.

The compositions of the present invention may comprise a mixture of two or more different types of amino acid surfactants.

In some preferred embodiments the personal care compositions of the present invention includes an isethionate surfactant.

Preferably the personal care compositions of the present invention include a substituted isethionate compound.

The personal care compositions of the present invention may suitably include a compound of formula (X):

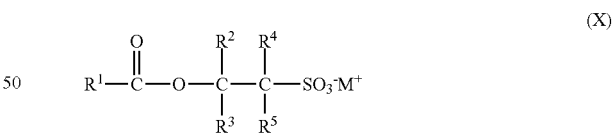

wherein $R^1$ represents a $C_{5-39}$ substituted or unsubstituted hydrocarbyl group;
each of $R^2$, $R^3$, $R^4$ and $R^5$ independently represents a hydrogen atom or a $C_{1-4}$ alkyl group and
wherein at least one of $R^2$, $R^3$, $R^4$ and $R^5$ is not hydrogen and $M^+$ represents a cation.

Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group.

Preferably $R^1$ is a $C_{5-39}$ alkyl or alkenyl group, preferably a $C_{5-35}$ alkyl or alkenyl group, suitably a $C_7$ to $C_{29}$ alkyl or alkenyl group, more preferably a $C_{7-23}$ alkyl or alkenyl group, most preferably a $C_{9-19}$ alkyl or alkenyl group, for example a $C_9$ to $C_{17}$ alkyl or alkenyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the present invention may include a mixture of more than one compound of formula (VI). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is alkyl (suitably methyl) and $R^2$, $R^3$ and $R^4$ are all hydrogen.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a potassium cation, or, especially, a sodium cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (VI) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (X) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably methyl.

In such preferred embodiments the composition of the present invention preferably comprises the reaction product of sodium methyl isethionate and a fatty acid, that is a compound of formula (XI):

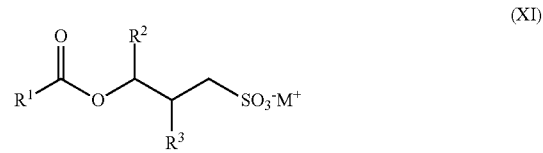

in which one of $R^2$ and $R^3$ is methyl and the other is hydrogen. Mixtures of these isomers are especially preferred.

In some embodiments the personal care composition of the present invention comprises one or more of sodium lauryl methyl isethionate, sodium cocyl methyl isethionate and sodium oleoyl methyl isethionate.

Most preferably the personal care composition of the present invention comprises sodium lauryl methyl isethionate and/or sodium cocoyl methyl isethionate. Sodium lauryl methyl isethionate is especially preferred.

In some preferred embodiments the present invention provides a personal care composition comprising a compound of formula (I) and a compound of formula (X).

In some embodiments the present invention provides personal care compositions comprising a compound of formula (I) and a compound of formula (XI).

In some embodiments the present invention provides a personal care composition comprising a compound of formula (III) and a compound of formula (XI).

In some embodiments the present invention provides a personal care composition comprising a compound of formula (IV) and a compound of formula (XI).

Suitably the present invention may comprise a personal care composition comprising a compound of formula (I) and a compound of formula (XI) in a weight ratio of from 100:1 to 1:100, preferably from 50:1 to 1:50, more preferably from 20:1 to 1:20, most preferably from 10:1 to 1:10.

The personal care compositions of the present invention may include one or more further ingredients. These may suitably be selected from components that are typically known for use in personal care compositions. For example the composition may comprise one or more emollients, dyes, fragrances, chelating agents For example the composition may comprise one or more emollients, dyes, fragrances, chelating agents, thickeners, conditioners, thickening agents, preservatives, antimicrobials, sequestrants, vitamins and derivatives thereof, sunscreens, desquamation actives, anti-wrinkle/anti-atrophy actives, anti-oxidants, skin soothing agents/skin healing agents, skin lightening agents, skin tanning agents, anti-acne medicaments, essential oils, sensates, pigments, pearlescent agents and interference pigments.

Other optional materials can be those materials approved for use in cosmetics and that are described in the CTFA Cosmetic Ingredient Handbook, Second Edition, The Cosmetic, Toiletries, and Fragrance Association, Inc. 1988, 1992.

According to a fourth aspect of the present invention there is provided a concentrated surfactant composition comprising a compound of formula (I).

The concentrated surfactant composition preferably comprises at least 20 wt % of surfactants in total. By this we mean to include compounds of formula (I) and any other surfactant compounds which may be present. Preferably the concentrated composition comprises at least 25 wt % in total of surfactant compounds, preferably at least 30 wt %, suitably at least 35 wt %, preferably at least 40 wt %, for example at least 45 wt %.

The concentrated surfactant composition may comprise up to 90 wt % in total of surfactant compounds, suitably up to 80 wt %, preferably up to 75 wt %, suitably up to 70 wt %, for example up to 65 wt % or up to 60 wt %.

In some embodiments the concentrated surfactant composition of the fourth aspect of the present invention comprises a compound of formula (I) and one or more further surfactant compounds.

Such concentrated surfactant compositions and concentrated surfactant premixed compositions are very useful for formulators.

Suitably the concentrated surfactant composition of the fourth aspect comprises at least 5 wt % of a compound of formula (I). Suitably the concentrated surfactant composition comprises at least 10 wt % or at least 15 wt % of a compound of formula (I).

In embodiments in which the compound of formula (I) is the main or only surfactant present in the concentrated composition it may be present in an amount of at least 20 wt %, for example at least 25 wt % or at least 30 wt %.

Suitably the compound of formula (I) is present the concentrated surfactant composition of the fourth aspect in an amount up to 90 wt %, suitably up to 80 wt %, preferably up to 70 wt %.

The concentrated surfactant composition of the fourth aspect may suitably be prepared by admixture of the surfactant component of the first aspect with a diluent and/or one or more further surfactants.

The concentrated surfactant composition is preferably an aqueous composition.

According to a fifth aspect of the present invention there is provided the use of a compound of formula (I) as a surfactant compound.

By this we mean to include any use as a detergent, wetting agent, emulsifier, foaming agent or dispersant.

In especially preferred embodiments the fifth aspect of the present invention provides the use of a compound of formula (I) as a mild surfactant in a personal care composition.

According to a sixth aspect of the present invention there is provided the use of a compound of formula (I) in the preparation of a personal care composition.

The sixth aspect may provide the use of a surfactant component of the first aspect in the preparation of a personal care composition.

The sixth aspect may provide the use of a concentrated surfactant composition of the fourth aspect in the preparation of a personal care composition.

According to a seventh aspect of the present invention there is provided a method of cleansing the skin and/or hair, the method comprising contacting the skin and/or hair with a composition comprising a compound of formula (I).

The method suitably involves wetting the skin and/or hair, applying the composition comprising a compound of formula (I) to the skin and/or hair, and rinsing the composition from the skin and/or hair.

A particular advantage of the compounds of formula (I) is that they are high foaming and produce a tight, dense foam. Thus the present invention may provide the use of a compound of formula (I) to provide a tight, dense foam.

The present invention may provide a high foaming composition, suitably a personal care composition comprising a compound of formula (I).

Thus, in an especially preferred embodiment the present invention may provide the use of a compound of formula (I) as a mild, high foaming surfactant in a personal care composition.

The present invention may further provide the use of a compound of formula (I) as an antioxidant or as a food supplement.

The present invention may provide the use of a compound of formula (I) as a health supplement.

The present invention may provide a compound of formula (I) for use as a medicament.

Any feature of any aspect of the invention may be combined with any feature of any other aspect.

Preferred features of the compound of formula (I) in the second, third, fourth, fifth, sixth, seventh and further aspects are as defined in relation to the first aspect.

The present invention will now further be defined with reference to the following non limiting examples.

EXAMPLE 1

Synthesis of Ascorbyl Monolaurate (Comparative)

7.5 g Ascorbic acid (42 mmol) and 0.3 g 4-Dimethylaminopyridine were weighed into a 500 ml beaker. 250 ml de-ionised water was added and reaction stirred. The pH was increased to 9.5 using 50% NaOH and reaction cooled to 0° C. 9.28 g Lauroyl chloride (42 mmol) was added dropwise over 10 minutes whilst the pH was maintained at 9.5-10. After full addition the reaction was allowed to warm to room temperature and left to stir for 2 hr. The pH was reduced to 2 using conc. HCl acid to precipitate the product. The white solid was filtered off and dried. Yield was 87%.

EXAMPLE 2

Synthesis of Ascorbyl Monolaurate Sulphate Solution 1.03 g ascorbyl monolaurate (2.8 mmol) was weighed into 100 ml beaker and 50 ml ether added. 0.33 g Chlorosulphonic acid (2.8 mmol) was added and the reaction stirred for 1 h. The reaction was then purged for 15 minutes with $N_2$. 20 ml de-ionised water and 4 g NaOH (50 wt %) were added. The ether was allowed to evaporate.

EXAMPLE 3

Comparative Foam Heights

A 1 wt % surfactant solution was prepared. The foam heights were measured using an in house foaming test and the results were compared with those obtained using a composition comprising 1 wt % Sodium Laureth Sulphate (3EO) [SLES]. The percentage increases in foam compared to SLES are shown in table 1.

|  | Relative foam height compared to SLES as % |
|---|---|
| Sodium Laureth Sulphate (3EO) | 100 |
| Compound 1 - Lauroyl Ascorbic acid (comparative) | 32 |

-continued

| | Relative foam height compared to SLES as % |
|---|---|
| Compound 2 - Lauroyl Ascorbate Sulphated | 105 |

EXAMPLE 4

An in house qualitative test based on the Zein test was used to assess irritancy/mildness of a 1% surfactant solution. In this test, Compound 2 was found to be milder than many commercially available personal care surfactants including Sodium Laureth Sulfate (3EO) [SLES].

The invention claimed is:

1. A composition comprising one or more compounds of formula (I):

$$\underset{R^1}{\overset{O}{\|}}\underset{R^2}{C}$$ (I)

wherein $R^1$ is a $C_5$ to $C_{39}$ alkyl or alkenyl group and $R^2$ is a group of formula (a)

(a) structure with YO, OZ, WO, XO substituents on furanone ring wherein one of W, X, Y and Z is a covalent bond and the remaining groups are independently selected from H, M, $SO_3M$ and a further group of formula $R^1CO$ provided at least one of W, X, Y and Z is $SO_3M$; and each M is independently a hydrogen ion, an ammonium ion or a metal ion; and one or more of sodium lauroyl methyl isethionate sodium cocoyl methyl isethionate or sodium oleoyl methyl isethionate.

2. The composition according to claim 1 which is a personal care composition.

3. The composition according to claim 2 selected from shampoo, a shower gel, a toothpaste, a moisturiser, a shaving foam or gel, a hand wash, a body wash, a bath foam, a bubble bath, a soap bar, a liquid soap, a toilet bar, a facial cleanser, a skin cleanser and a make-up remover.

4. The composition according to claim 1 which is of low irritancy to the skin and/or eyes.

5. The composition according to claim 1 which is high foaming.

6. The composition according to claim 1 which comprises a compound of formula (III):

(III) structure with HO, OH, $MO_3SO$ substituents and/or a compound of formula (IV):

(IV) structure with HO, $OSO_3M$, HO substituents

7. The composition according to claim 1 wherein $R^1$ is a $C_9$ to $C_{15}$ alkyl or alkenyl group or mixtures thereof.

8. A method of cleansing the skin and/or hair, the method comprising:

wetting the skin and/or hair:

applying a composition comprising one or more compounds of formula (I) to the skin and/or hair; said compound having the formula:

$$\underset{R^1}{\overset{O}{\|}}\underset{R^2}{C}$$ (I)

wherein $R^1$ is a $C_5$ to $C_{19}$ alkyl or alkenyl group and $R^2$ is a group of formula (a)

(a) structure with YO, OZ, WO, XO substituents on furanone ring wherein one of W, X, Y or Z is a covalent bond and the remaining groups are independently selected from H, M. $SO_3M$ or $R^1CO$ provided at least one of W, X, Y or Z is $SO_3M$; and each M is independently a hydrogen ion, an ammonium ion or a metal ion; and rinsing the composition from the skin and/or hair, wherein when used in the method, composition produces tight, long lasting foam having a reasonable foam volume.

9. The method according to claim 8, wherein the one or more compounds comprise a compound of formula. (III):

(III) structure with HO, OH, $MO_3SO$ substituents and/or a compound of formula

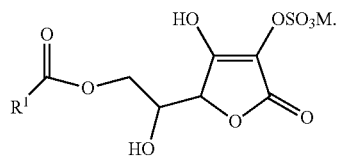

10. The method according to claim 8, wherein $R^1$ is a $C_9$ to $C_{15}$ alkyl or alkenyl group or mixtures thereof.

11. The method according to claim 8, wherein said composition further comprises one or more surfactants selected from the group consisting of: anionic, cationic, non ionic and amphoteric surfactants.

12. The method according to claim 8. wherein said composition is in the form of a shampoo, a shower gel, a shaving foam or gel, a hand wash, a body wash, a bath foam, a bubble bath, a soap bar, a liquid soap, a toilet bar, a facial cleanser, a skin cleanser or a make-up remover.

13. The method according to claim 8, wherein said composition is of low irritancy to the skin and/or eyes.

14. The method according to claim 8, Wherein said composition further comprises a surfactant selected from the group consisting of: alkyl or alkenyl sulfates, alkyl or alkenyl ether sulfates, taurates, isethionates, acyl substituted amino acids, sarcosinates and sulfosuccinates.

15. The method according to claim 8, wherein said composition further comprises one or more isethionate selected from the group consisting of: sodium lauroyl methyl isethionate, sodium cocoyl methyl isethionate and sodium oleoyl methyl isethionate.

\* \* \* \* \*